United States Patent [19]
Brewer

[11] Patent Number: 5,908,783
[45] Date of Patent: Jun. 1, 1999

[54] ALTERNATING LYSINE-ALANINE COPOLYMER SUBSTRATE FOR PROMOTING NEURON SURVIVAL AND AXON GROWTH

[75] Inventor: Gregory J. Brewer, Springfield, Ill.

[73] Assignee: Southern University, Bd. of Trustee, Springfield, Ill.

[21] Appl. No.: 08/984,742

[22] Filed: Dec. 4, 1997

[51] Int. Cl.$^6$ .............................. C12N 5/08; C12N 5/06; C12N 5/00
[52] U.S. Cl. .......................... 435/368; 435/353; 435/395; 435/402
[58] Field of Search ................................ 435/395, 396, 435/402, 368, 353

[56] References Cited

U.S. PATENT DOCUMENTS

| | | | |
|---|---|---|---|
| 4,415,492 | 11/1983 | de Weck et al. | 260/112.5 R |
| 5,147,399 | 9/1992 | Dellon et al. | 623/12 |
| 5,444,150 | 8/1995 | Inman et al. | 530/300 |
| 5,543,498 | 8/1996 | Fishman et al. | 530/328 |
| 5,656,605 | 8/1997 | Hansson et al. | 514/21 |

OTHER PUBLICATIONS

Banker et al., "Rat hippocampal neurons in dispersed cell culture", Brain Research, 1977, 126, pp. 397–425.

Brewer et al., "Survival and growth of hippocampal neurons in defined medium at low density: advantages of a sandwich culture technique or low oxygen", Brain research, 1989, 494, pp. 65–74.

Yong et al., "Comparison of six different substrata on the plating efficiency, differentiation and survival of human dorsal root ganglion neurons in culture", Dev. Neursci., 1988, 10, pp. 222–230.

Chu et al, "Polyamines promotes regeneration of injured axons of cultured rat hippocampal neurons", Brain Research, 1995, 673, pp. 233–241.

Kielland et al., "Water–soluble lysine–containing polypeptides", Can. J. Chem. 1978, 56 (20), pp. 2650–2656.

Brack et al., "B structures of alternating polypeptides and their possible prebiotic significance," *Nature*, vol. 256, 1975, pp. 383–387.

Johnson, "Synthesis, Structure, and Biological Properties of Sequential Polypeptides," *Journal of Pharmaceutical Sciences*, 1974, pp. 313–327.

Varani et al., "Use of recombinant and synthtic peptides as attachment factors for cells on microcarriers," *Cytotechnology*, vol. 13, 1993, pp. 89–98.

Yaron et al., "Sequential Polypeptide (LYS–ALA–ALA)n, Synthesis and Conformation," *Israel J. Chem.*, vol. 8, 1970, p. 180p.

*Primary Examiner*—Sandra E. Saucier
*Assistant Examiner*—Vera Afremova
*Attorney, Agent, or Firm*—Rockey, Milnamow & Katz

[57] ABSTRACT

Substrates containing a copolymer of sequentially alternating lysine and alanine residues are provided. The use of those substrates for promoting neuron survival and axon growth are also provided.

12 Claims, 4 Drawing Sheets

A) Tau Fiber Length

B) Tau Immunoreactivity/Neuron

ALTERNATING LYSINE-ALANINE COPOLYMER SUBSTRATE FOR PROMOTING NEURON SURVIVAL AND AXON GROWTH

TECHNICAL FIELD OF THE INVENTION

The field of the present invention is copolymer substrates for use in cell culture. More particularly, the field of the present invention relates to substrates containing copolymers of alternating lysine and alanine residues and the use of such substrates for promoting neuron survival and axon growth.

BACKGROUND OF THE INVENTION

It is known in the art to use polymers as substrates for neuron cell cultures of the central nervous system (CNS). The most common method utilizes polylysine, a homopolymer, to coat glass and plastic surface [see Banker & Cowan, *Rat hippocampal neurons in dispersed cell culture*, Brain Res., 126:397–425 (1977); Mattson et al., *Outgrowth-regulating actions of glutamate in isolated hippocampal pyramidal neurons*, J. Neurosci., 8:2087–2100 (1988); Brewer & Cotman, *Survival and growth of hippocampal neurons in defined medium at low density: advantages of a sandwich culture technique or low oxygen,* Brain Res., 494:65–74 (1989)]. Polylysine is considered to be efficacious and economical.

However, it is unknown whether the cationic structures of polylysine substrates are able to promote neuron adhesion and differentiation. In fact, polylysine does not appear to mimic adhesive brain proteins that are known to stimulate differentiation. These proteins that stimulate differentiation, including laminin, pleiotrophin (HB-GAM), L1 and N-CAM, are distinguishable from polylysine because they do not contain sequences of polylysine or other basic residues. Unfortunately, the high costs of production, isolation and purification associated with these large cell-adhesion molecules cause researchers to turn to synthetic polymers to accomplish neuron adhesion and differentiation.

Copolymers of lysine and alanine (LAS) have not previously been reported as effective substrates for neurons or other cells. Other polypeptides containing the integrin binding site for fibronectin, RGD (Varani et al., 1993) have proven to be effective substrates for fibroblasts and other cells A ten-residue peptide fragment of laminin promotes neurite outgrowth (Liesi et al., 1989). An antibody to a 14 residue peptide from the L1 adhesion molecule increases neuritogenesis (Appel et al., 1995), probably through an integrin mediated receptor (Montgomery et al., 1996). Short polypeptides of lysine and alanine have been shown to bind strongly to DNA (Takeuchi et al., 1991), but this is not likely to be the mechanism by which substrate-bound LAS stimulates survival and axongenesis in neurons. LAS may be a model for naturally occurring polyamine such as spermidine, spermine and putrescine (Morrison et al., 1995). B27 medium, as well as the N2 medium of Bottenstein and Sato (1979) contains putrescine. Chu et al. (1995a) have shown that the butanediamine structure of these polyamine is required for enhanced survival of hippocampal neurons when added to the culture medium. Similar additions of any of the three of these polyamines promoted neurite elongation (Chu et al., 1994) or regeneration of injured hippocampal axons in cultures growing on poly-lysine (Chu et al., 1995a). A BLAST search of the NCBI protein data base revealed no proteins with and Ala-Lys-Ala-Lys sequence.

Therefore, there is a need in the art for a polymer substrate that is inexpensive while also having the ability to promote neuron survival and axon growth.

BRIEF SUMMARY OF THE INVENTION

In one embodiment, the present invention is for a novel substrate containing a copolymer of sequentially alternating lysine-alanine amino acid residues. The copolymer has molecular weight less than about 30,000 Daltons. The substrate promotes neuron survival and axon growth. Still further, the present invention is directed to a process for promoting neuron survival and axon growth using such substrates.

In a serum-free medium optimized for survival of hippocampal neurons grown on substrates of poly-D-lysine, 13% more neurons survived on substrates to which a sequentially alternating copolymer of lysine and alanine (LAS) was applied. The effect was specific for the sequential polymer, in contrast to the random copolymer of lysine and alanine. This shows that average cationic charge density is not as important as the spacing of these charges. Furthermore, immunostaining for the axon-associated microtubule associated protein, tau, indicates a two-gold higher rate of fiber growth on LAS. The somatodendritic cytoskeletal component MAP2 is also increased in cells cultured on LAS. This shows that cytoskeletal differentiation in general and axon formation in particular are likely stimulated by the LAS substrate. Scanning electron microscopy supports this conclusion.

The LAS copolymer is useful for studying assembly of the axonal cytoskeleton and regeneration after axotomy. Tubes or other substrates coated with LAS can also serve as in vivo splints to reconnect damaged circuits or guide connections to neurosprostheses. The high survival and faster axonogensis can also hasten synaptogensis.

BRIEF DESCRIPTION OF THE DRAWINGS

In the drawings that form a portion of the sepcification.

DETAILED DESCRIPTION OF THE INVENTION

Figure 1:
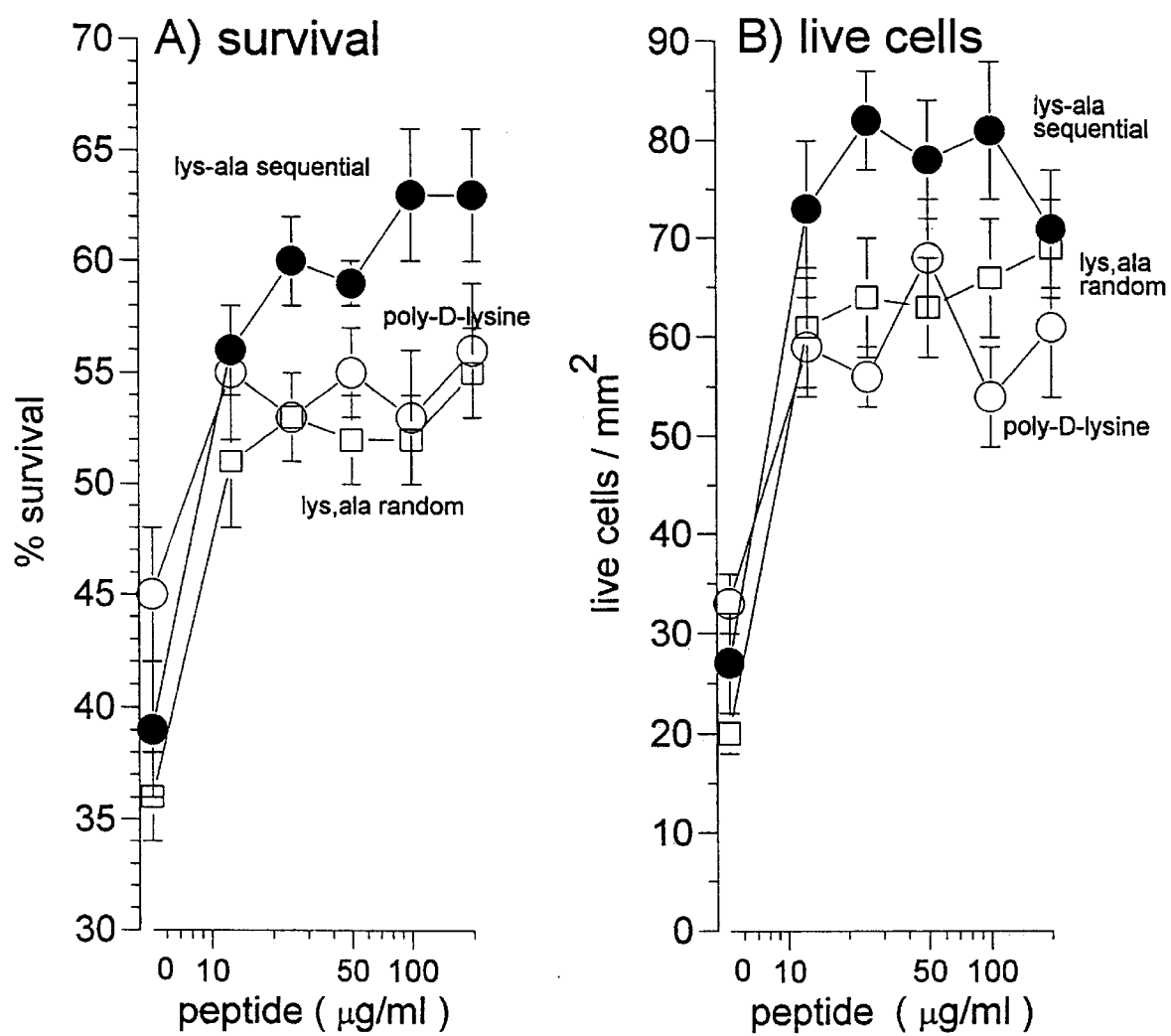
FIGS. 1A and B. Show that survival and viability are higher for neurons grown on substrates coated with LAS. Substrates were coated with one of three polypeptides at the indicated concentrations: lysine alanine sequential polymer (solid circles), poly-D-lysine (open circles), or lys, ala random copolymer (open squares). (A) survival (live cells/total cells) and (B) live cells were measured after 4 days. ANOVA indicates survival on lys-ala is significantly larger than survival on poly-D-lysine (p=0.006).

In one aspect, the present invention provides a substrate for cell culture, which substrate includes a copolymer of sequentially alternating lysine and alanine residues. As used herein, the phrase "sequentially alternation" means a sequence of amino acid residues having only lysine (Lys) and alanine (Ala) residues, which lysine and alanine residues exist as repeating pairs. The copolymer can, therefore, be represented by the formula (Lys-Ala)$_n$ or the formula (Ala-Lys)$_n$, where n is an integer greater than zero.

Preferably, the copolymer has a molecular weight of less than about 30,000 Daltons (i.e., there are less than about 150 repeating Lys-Ala pairs). More preferably, the copolymer has a molecular weight of less than about 20,000, 10,000, 5,000, 2,500, 1,500, or 1,000 Daltons. The copolymer of this invention can be linear or branched. Means for making Lys-Ala copolymers are well known in the art.

The substrate further includes a solid support. The solid support is coated with the copolymer such that the coated surface is exposed to cells or tissue for culture. Any solid support known in the art can be used. Exemplary and preferred solid supports are glass and plastic such as polystyrene. Means for coating a solid support with copolymers are well known in the art.

A substrate of this invention can be used to culture any cell. The substrate has particular utility with neural cells and tissues. The effects of Lys-Ala copolymer substrates on neural cell growth and viability were studied. Three types of substrates were prepared by adsorption of polypeptides from varying aqueous concentrations: (1) poly-D-lysine, (2) a random copolymer of lysine and alanine (Lys,Ala), and (3) a sequential copolymer of lysine and alanine (Lys-Ala).

All polypeptides were obtained from Sigma Chemical Co. (St. Louis). The following random copolymers were of average molecular weight 20,000–50,000 Daltons and were filter sterilized before use; Lys,Ala 3:1 (P1151), Lys,Ser 3:1 (P9160), Lys,Tyr 4:1 (P4659), Lys,Phe 1:1 (P3150). Lys,Tyr 1:1 (P4247) was of average molecular weight 50,000–150,000 Daltons. The following were supplied as gamma irradiated material and were not filter sterilized: poly-D-lysine (70,000–150,000 MW, P6407), random Lys,Ala 1:1 (P4024) and Lys-Ala sequential copolymer (LAS, average MW 14,500, P5209). Sequential polymers were synthesized according to Engel et al. (1966).

Peptides were dissolved at 1 mg/ml in 18 megohm water and stored at −20° C. After thawing and dilution to 50 μg/ml, unless otherwise indicate, either 0.1 ml was applied to each 12 mm D glass coverslip (Assistent brand, Carolina Biologicals, Burlington) or 0.3 ml was added to each well of 24 well cell culture plate (Corning 4,30262). After incubation overnight at room temperature, substrates were rinsed once with equal volumes of sterile water and allowed to dry.

To obtain a quantitative standard of peptide, either poly-D-lysine or LAS were applied as 0, 1.25, 2.5, 5 and 10 μg in 0.1 water, 20 μl 10 mM KCN and 10 μl 10 mM Atto-Tag-CBQ (molecular Probes, Eugene). After 1 hr. at room temperature, amino-derivatives were measured by fluorescence excitation at 450 nm and emission at 550 nm (Perkin-Elmer LS50B). Analysis of both standards were collinear with a correlation coefficient of 0.94 by regression analysis. To determine the amount of peptide that was adsorbed from the usual aqueous solution, the same procedure was conducted on triplicate sample of peptides that were adsorbed to glass slips from a 5 μg sample and rinsed with water.

To quantify the amount of peptide attached to substrates by adsorption from an aqueous solution, we first created a standard series of known amount of peptides that were dried onto the substrates. The amino acids were released from substrates by hydrolysis and detected by fluorescent derivatization of amino groups. In the typical application of 5 μg of poly-D-lysine or LAS from aqueous solution, 2.9±0.7 μg of poly-D-lysine or 2.3±0.8 μg of LAS (mean±S.E., n=3) were recovered and detected. These values indicate that about 60% of the peptide that was applied to glass coverslips remained after rinsing and was available for cell attachment. Although these values were not statistically different, the 21% lower value for LAS was 94% of theoretical on a molar basis. This is because hydrolyzed LAS has only 75% of the amino groups found in hydrolyzed poly-D-lysine.

Neurons were isolated from E18 Sprague-Dawley rats as described (Brewer et al., 1993). Cells were plated in 2% B27 in Neurobasal (Life Technologies, Gaithersburg), 0.5 mM glutamine, 25 μM glutamate at concentration between 50 and 100 cells/mm$^2$ of substrate. Cultures were incubated 37° C. in a humidified atmosphere of 5% $CO_2$, 9% $O_2$. For experiments lasting longer than 4 days, one-half of the medium was replaced with fresh medium without glutamate twice a week. Survival was assayed with fluorescein diacetate and propidium iodide (Brewer et al., 1993).

After 4 days of culture, live and dead cells were counted as a measure of survival. FIG. 1 shows that survival and the number of live neurons were both consistently higher for Lys-Ala sequential copolymer (LAS) substrate at concentrations between 20 and 100 μg/ml. An average of 5 neuron preparations showed a 13% higher survival for LAS over poly-D-lysine (paired two-tailed t-test, p=0.01).

Survival on the random copolymer of Lys and Ala was similar to conventional polylysine. Earlier work showed no differences between poly-D-lysine and poly-L-lysine and no effect of molecular weight of polylysine over the range of 30,000 to 300,000 D (Brewer & Cotman, 1989). Other random co-polymers examined produced either inhibition of survival: Lys,Ser (3:1), Lys,Ala (3:1), Lys,Tyr (1:1) or no difference from polylysine: Lys,Tyr (1:1).

Cells for staining with anti-tau and anti-MAP2 antibodies were rinsed free of medium with warm PBS and fixed for 10 min. at room temperature with 4% paraformaldehyde in PBS. After rinsing twice with PBS, cells were permeabilized and non-specific sites were blocked for 10 min. With 0.5% Triton X-100, 5% normal goat serum, 1% bovine serum albumin in PBS. Cells were incubated overnight at 4° C. with rabbit anti-tau (Sigma T6402, diluted 1:1200) and mouse anti-MAP2 (Sigma M4403, diluted 1:50) in the blocking solution with 0.05% Triton X-100. After rinsing four times with PBS, secondary antibodies were incubated for 60 min.: affinity purified Cy2-conjugated goat anti-rabbit IgG (heavy+light chains) diluted 1:4000 (Jackson). After rinsing four times in PBS, slips were mounted in Aquamount (Scientific Products) and photographed with Ektachrome P800 film through a Nikon 60Z/1.4 n.a. oil immersion objective and Nikon B1A and G1B filters. For controls, the primary antibodies were replaced with normal rabbit serum and a mouse monoclonal against mouse mammary tumor virus (courtesy of Walter Myers). For measuring the length of fibers immunolabeled for tau, isolated cells were imaged through a 20× objective, digitized through an Ikegami Newvicon camera and a Data Translation 3155 frame grabber into a Pentium 133 MHZ PC. The longest fiber of a least 10 cells was traced with a mouse and the linear extent measured with Global Lab Image software (Data Translation, Marlboro, Mass.).

The morphology of neurons grown on LAS was dramatically different from those grown on conventional poly-D-lysine. Fibers emanating from the soma were of more uniform caliber, longer and thinner on LAS than on PDL. Cells were immunostained to determine whether these axon-like qualities were associated with the characteristic cytoskeletal protein, tau, or the somatodendritic protein MAP2 (Kosik & Finch, 1987). Neurons on LAS showed a typical higher proportion of narrow fibers selectively labeled for tau as well as labeling go tau in the nucleus (Thurston et al., 1996) and somatodendritic labeling of tau and MAP2. Neurons on poly-D-lysine showed mostly coincident labeling of tau and MAP2.

Figure 2:
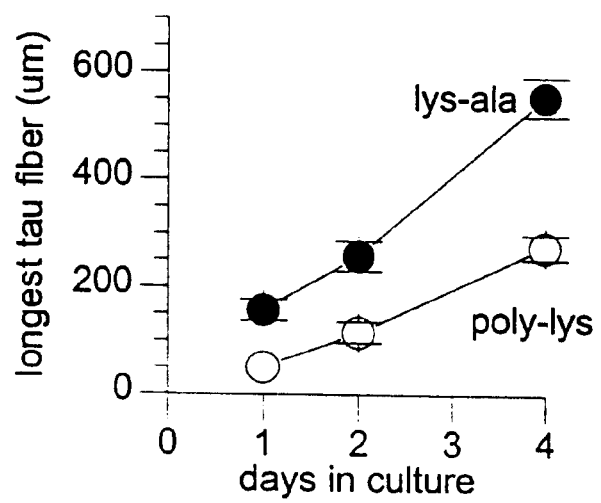
FIGS. 2A and B. Show that (A) the length of longest tau reactive fiber is greater for neurons cultured on LAS (solid circles) compared to ply-D-lysine (open circles). The difference is seen for neurons in culture for 1, 2 or 4 days. Representative of 3 experiments. At longer times, (B) total immunoreactive area for tau was greater for neurons cultured on LAS (solid circles) compared to poly-D-lysine (open circles).
Figure 2:
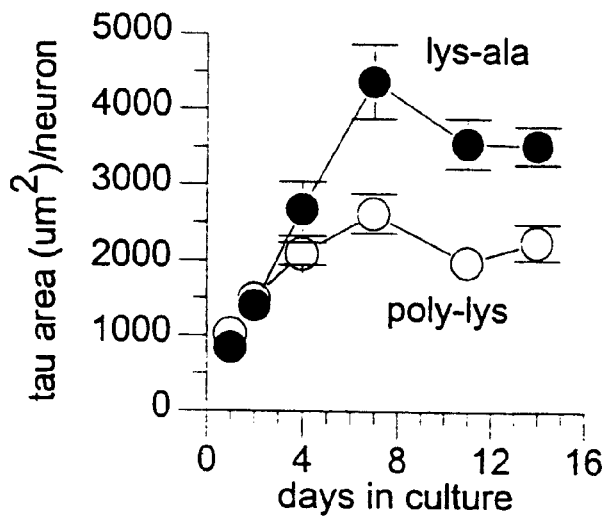

To answer the question whether the apparent increase in tau is due to increased tau expression or decreased MAP2 expression LAS substrates, images were digitized. The time course of axon-like differentiation was also determined. Development of tau immunoreactivity was measured as the length of the longest tau-staining fiber of individual cells. FIG. 2A shows that as early as one day in culture, tau-fibers were 3-fold longer for cells growing on LAS, compared to poly-D-lysine. The difference narrowed to 2-fold at longer times by day 4. At day 7, 11 and 14, the density of tau fibers was too high to discriminate individual fibers. However, total tau immunoreactivity peer neuron could be measured. FIG. 2B shows that total tau expression in neurons on LAS exceeds that of neurons on poly-D-lysine beginning on day 4 and approaches two-fold higher thereafter.

Figure 3:
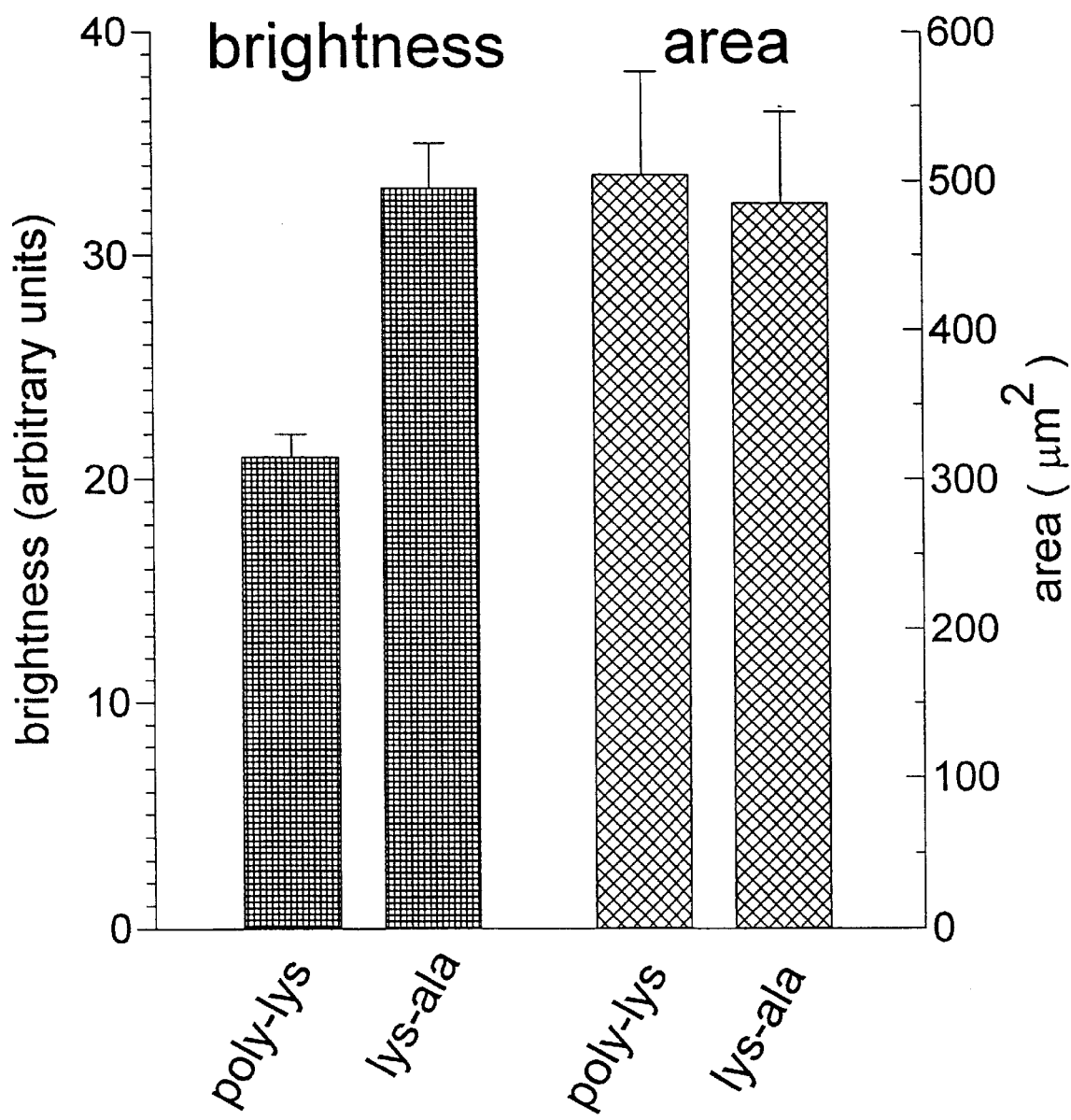
FIG. 3. Shows that after 4 days in culture, MAP2 immunoreactivity is greater for neurons cultured on LAS compared to poly-D-lysine. Fluorescent mean brightness/cell on the LAS substrate was significantly greater that on the poly-D-lysine substrate (t test, p=0.0003, n>10). The fluorescent area/cell was not significantly different on the two substrates.

Digital analysis of MAP2 indicated a significantly larger antigen concentration for neurons grown on LAS compared to poly-D-lysine (FIG. 3). This increases in MAP2 density occurred without a change in immunoreactive area/cell.

Cells on coverslips were rinsed twice with Hanks buffered salts (HBS, Life Technologies) and fixed for 20 min. at room temperature in 2% glutaraldehyde, 0.12 M sucrose in HBS. After rinsing twice with PBS, cells were dehydrated for 1 min. With 10% ethanol in water, followed by 30, 50, 70, 85, 95 (twice) and 100% (trice) ethanol. Samples were dried at the critical point of $CO_2$, with a 10 min. purge. Cells were examined on a Hitachi S500 at 20 kV and 5 mm working distance.

Neurons grown on poly-D-lysine adhered tightly to the substrate with a thin veil of cytoplasm. Growth of axon-like narrow fibers appeared limited compared to similar cultures on substrates of LAS. Cells on LAS showed less spreading of cytoplasm onto the substrate than cells on poly-D-lysine. Fibers were also longer on LAS than poly-D-lysine.

To determine the degree of branching at lysine-residues, reductive methylation was performed by modification of the method of Kielland et al. (1978). Triplicate samples of peptides were dissolved at 1 mg/ml in 0.2 M sodium borate, ph 9.0. One ml aliquots were treated at 24° C. with 0.01 ml 2 M borane-pyridine (Aldrich 17,975-2) in methanol. After ten min., 0.01 ml 2.5 M formaldehyde, 0.2 M sodium borate, pH 9.0 was added. This sequence of additions of borane-pyridine and formaldehyde was repeated three more times, followed by a final addition of borane-pyridine. After acidification, remaining free amino groups were measured by reaction with trinitrobenzene sulfonic acid (Cuatrecasa, 1970). Amino acid analysis was performed on a Beckman Model 126AA System Gold after hydrolysis in 0.05 ml 6 N HCI at 115° C. for 21 hr.

The solution conformation of LAS, poly-D-lysine and random Lys,Ala polymer were determined by circular dichroism. For circular dichroism, samples were dissolved at 0.1 mg/ml in 10 mM sodium phosphate, 150 mM NaCl, pH 7.4. Spectra were collected from three scans on a Jasco J-600 spectropolarimeter.

Figure 4:
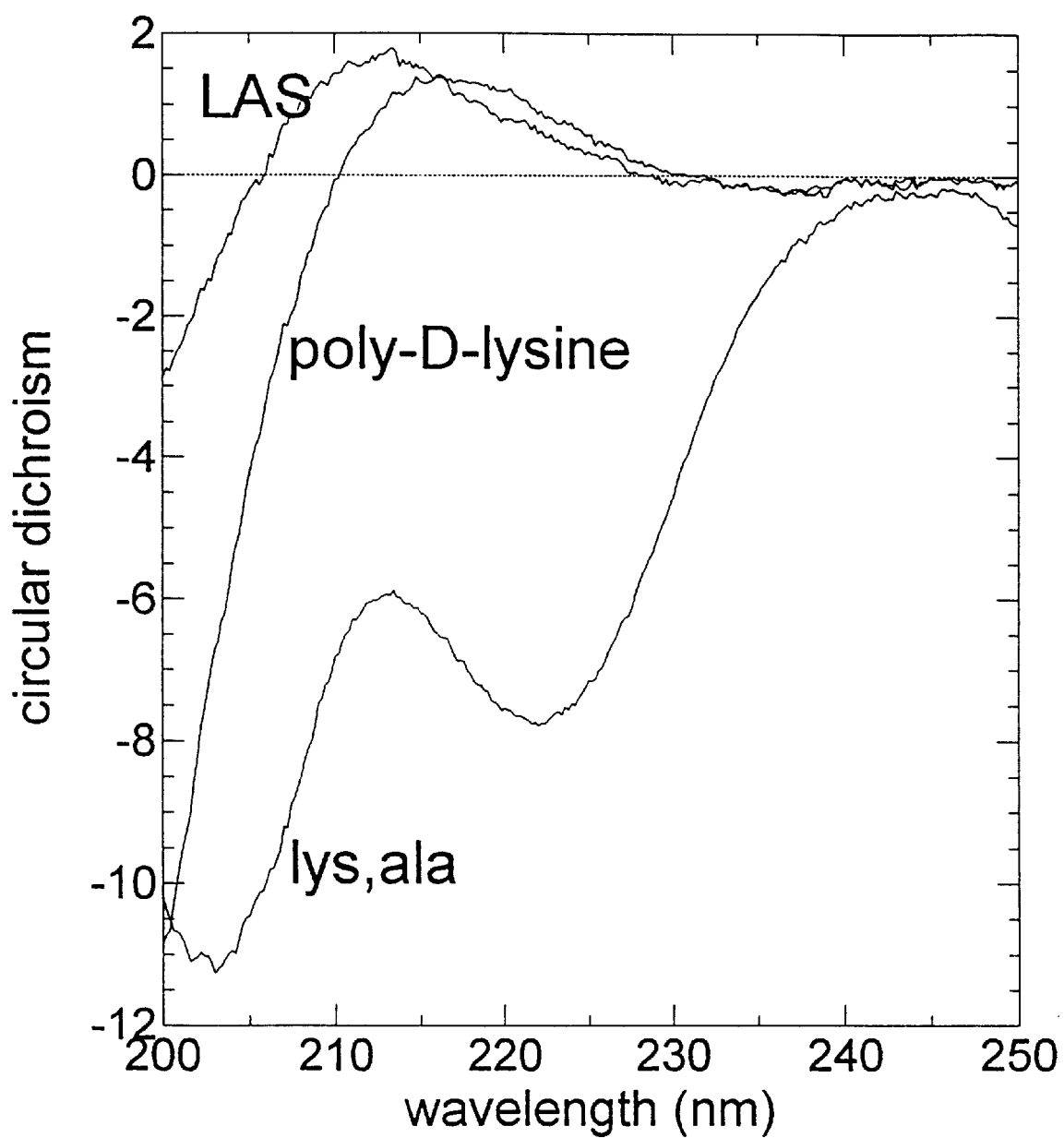
FIG. 4. Shows the circular dichroism spectra for (A) poly-D-lysine, (B) LAS, and (C) lys, ala random polymers at 0.1 mg/ml in 10 mM sodium phosphate, 150 mM NaCl, pH 7.4. The trough near 225 nm indicates some alpha-helical nature for lys, ala. The flat signal in the 220–240 nm range indicates random coil conformation.

FIG. 4 shows spectra characteristic of random coil conformation for both LAS and poly-D-lysine. In contrast, the peak near 222 nm indicates some alpha-helical content for the random polymer Lys, Ala.

The cell receptor that binds to poly-D-lysine or LAS is not known. It is not known whether the apparent 15% branching detected in LAS is important for the survival and cytoskeletal simulation. Circular dichroism studies show a random coil conformation for LAS and poly-D-lysine in PBS. However, the conformation on the substrate may be that of a beta sheet. In a beta sheet conformation of an alternating neutral and basic amino acid, the positive charges on the epsilon amino groups of lysines could align on one side of the sheet. The opposite side would be highly hydrophobic side chains of alanine. For a similar polymer of lysine and valine, Brace and Orgel (1975) found circular dichroism evidence for a beta-sheet structure at pH 2.3 with lysines on one side, space at 4.65 Å. A possible neuron receptor may involve chondroitin sulfate attached to a membrane plycoprotein, with sulfate groups spaced an average of 4 Å. The carboxyl and sulfate groups of heparin sulfate average 4 Å along the chain (Mulloy et al., 1993); a finding consistent with the x-ray structure for the complex of heparin and basic fibroblast growth factor (Faham et al., 1996). For this growth factor, lysines or arginines interact with sulfates of carboxylates at distances of 4.4 to 11 Å (R. Hileman, personal communication).

LAS is synthesized without protection of the lysine ε-amino group, which allows limited branching of he polymer. Amino acid analysis before and after reductive methylation was used to measure the degree of branching. Table 1, below, shows the equimolar composition of LAS and Lys, Ala before methylation. Table 1. Amino acid analysis before and after methylation for branch points (µmol/mg)

| sample | unmethylated | | methylated polymers | | | |
|---|---|---|---|---|---|---|
| | ala | lys | ala | lys | ε-N,N-dimethyl lys | % unmethylated[a] |
| poly—D—lys | | 4.4 | | <0.1 | 4.4 | <1 |
| lys,ala | 3.2 | 3.2 | 3.1 | <0.1 | 3.4 | <3 |
| LAS | 3.7 | 3.55 | 3.45 | 0.55 | 1.65 | 15 |

[a]% unmethylated = 100* lys after methylation/lys unmethylated

After methylation, all the original lysines were methylated for Lys,Ala and for poly-D-lysine, indicating no branching. For the LAS polymer, 15% of the lysines were not methylated, most likely because lysines in a branching structure are protected from methylation.

What is claimed is:

1. A substrate for growing neural tissue comprising a copolymer of sequentially alternation lysine and alanine residues having a molecular weight of less than about 30,000 Daltons and a solid substrate selected from the group consisting of glass and plastic.

2. The substrate of claim 1 wherein the copolymer has a molecular weight of less than about 20,000 Daltons.

3. The substrate of claim 1 wherein the copolymer has a molecular weight of less than about 15,000 Daltons.

4. The substrate of claim 1 wherein the copolymer has a molecular weight of less than about 10,000 Daltons.

5. The substrate of claim 1 wherein the copolymer has a molecular weight of less than about 5,000 Daltons.

6. The substrate of claim 1 wherein the copolymer has a molecular weight of less than about 2,500 Daltons.

7. The substrate of claim 1 wherein the copolymer has a molecular weight of less than about 1,500 Daltons.

8. The substrate of claim 1 wherein the copolymer is branched.

9. The substrate of claim wherein the solid substrate is coated with the copolymer.

10. The substrate of claim 1 wherein the plastic is polystyrene.

11. A method for promoting neuron viability comprising culturing the neuron on the substrate of claim 1.

12. A method for promoting growth of a neuron axon comprising culturing the neuron axon on the substrate of claim 1.

* * * * *